(12) United States Patent
Cappello

(10) Patent No.: US 12,343,384 B2
(45) Date of Patent: Jul. 1, 2025

(54) COMPOSITIONS FOR COSMETIC AND DERMATOLOGICAL USE

(71) Applicant: SEMIOCARE SAS, Paris (FR)

(72) Inventor: Serge Cappello, Tremblay en France (FR)

(73) Assignee: SEMIOCARE SAS, Paris (FR)

( * ) Notice: Subject to any disclaimer, the term of this patent is extended or adjusted under 35 U.S.C. 154(b) by 0 days.

(21) Appl. No.: 17/261,866

(22) PCT Filed: Jul. 19, 2019

(86) PCT No.: PCT/EP2019/069603
§ 371 (c)(1),
(2) Date: Jan. 20, 2021

(87) PCT Pub. No.: WO2020/016450
PCT Pub. Date: Jan. 23, 2020

(65) Prior Publication Data
US 2021/0290737 A1    Sep. 23, 2021

(30) Foreign Application Priority Data
Jul. 20, 2018    (FR) ..................... 1856756

(51) Int. Cl.
| | | |
|---|---|---|
| A61K 38/40 | (2006.01) | |
| A61K 8/35 | (2006.01) | |
| A61K 8/44 | (2006.01) | |
| A61K 8/49 | (2006.01) | |
| A61K 8/64 | (2006.01) | |
| A61K 8/98 | (2006.01) | |
| A61K 9/00 | (2006.01) | |
| A61K 31/12 | (2006.01) | |
| A61K 31/198 | (2006.01) | |
| A61K 31/405 | (2006.01) | |
| A61K 35/20 | (2006.01) | |
| A61K 38/01 | (2006.01) | |
| A61P 17/00 | (2006.01) | |
| A61Q 19/08 | (2006.01) | |

(52) U.S. Cl.
CPC .............. *A61K 38/40* (2013.01); *A61K 8/35* (2013.01); *A61K 8/44* (2013.01); *A61K 8/492* (2013.01); *A61K 8/64* (2013.01); *A61K 8/986* (2013.01); *A61K 9/0014* (2013.01); *A61K 31/12* (2013.01); *A61K 31/198* (2013.01); *A61K 31/405* (2013.01); *A61K 35/20* (2013.01); *A61K 38/018* (2013.01); *A61P 17/00* (2018.01); *A61Q 19/08* (2013.01); *A61K 2800/522* (2013.01)

(58) Field of Classification Search
CPC ....... A01N 47/44; A01N 31/02; A61L 2/0088; A61L 2/18; A61L 2202/24
See application file for complete search history.

(56) References Cited

U.S. PATENT DOCUMENTS

| | | | | |
|---|---|---|---|---|
| 5,314,873 A | * | 5/1994 | Tomita | C07K 14/4732 435/68.1 |
| 5,750,149 A | * | 5/1998 | Gobbi | A61Q 19/00 530/832 |
| 2008/0045909 A1 | * | 2/2008 | Fossel | A61Q 19/08 604/290 |
| 2008/0317684 A1 | * | 12/2008 | Spann-Wade | A61P 17/02 424/59 |
| 2010/0092497 A1 | * | 4/2010 | Kanwar | A61K 31/593 514/2.5 |
| 2010/0272763 A1 | * | 10/2010 | Nakamura | A61Q 19/00 977/773 |
| 2011/0312892 A1 | * | 12/2011 | Balandras | A61K 38/1709 435/254.2 |
| 2013/0089572 A1 | | 4/2013 | Vanderhoof et al. | |

FOREIGN PATENT DOCUMENTS

| | | | | |
|---|---|---|---|---|
| CA | 2580372 A1 | 3/2006 | | |
| EP | 1997477 A1 | 12/2008 | | |
| JP | H03220130 A | 9/1991 | | |
| JP | 2009221157 A | * 10/2009 | | |
| WO | 9965329 A2 | 12/1999 | | |
| WO | 2004047566 A1 | 6/2004 | | |
| WO | 2006098625 A1 | 9/2006 | | |
| WO | WO-2007000651 A1 | * 1/2007 | ........... | A61K 31/355 |
| WO | 2008056983 A1 | 5/2008 | | |
| WO | 2015125067 A1 | 8/2015 | | |

OTHER PUBLICATIONS

English translation of JP2009221157A. English translation from Global Dossier. Retrieved on Oct. 20, 2023. (Year: 2023).*
International Search Report and Written Report, PCT/EP2019/069603, mailed Oct. 8, 2019.
Edriss et al. "Therapy of keloid and hypertrophic scars: a review" European Journal of Plastic Surgery, Springer, Berlin, DE, vol. 34, No. 6 Jul. 1, 2011 (Jul. 1, 2011), pp. 425-436 DOI:10.1007/S00238-011-0602-1ISSNI435-0130.

(Continued)

*Primary Examiner* — Doan T Phan
(74) *Attorney, Agent, or Firm* — Alleman Hall & Tuttle LLP

(57) ABSTRACT

The invention concerns a composition for cosmetic or dermatological use comprising an iron-binding glycoprotein and a casein hydrolysate, and optionally comprising colostrum, a precursor of nitric oxide, an antioxidant and serotonin or one of the precursors thereof.

18 Claims, No Drawings
Specification includes a Sequence Listing.

(56) References Cited

OTHER PUBLICATIONS

Callen J et al. "A systematic review of the safety of topical therapies for atopic dermatisis" The British Journal of Dermatology Feb. 2007 vol. 156 No. 2 Feb. 2007 (Feb. 2007) pp. 203-221 ISSN 0007-0963.
European Office Action, EP19742048.2, mailed Apr. 4, 2022, 7 pages.
Miclo, L. et al. "Characterization of alph-casozepine, a tryptic peptide from bovine alphas 1-casein with benzodiazepine-like activity" The FASEB Journal, Federation of American Societies for Experimental Biology, US, vol. 15, No. 10, Aug. 1, 2001 (Aug. 1, 2001), pp. 1780-1792, XP-002481109, ISSN: 0892-6638.

* cited by examiner

COMPOSITIONS FOR COSMETIC AND DERMATOLOGICAL USE

This application is a 35 U.S.C. § 371 US national stage entry of International Application number PCT/EP2019/069603, filed Jul. 19, 2019, and claims priority to French applications No. FR1856756 and FR1856756A filed Jul. 20, 2018. The contents of the aforementioned applications are incorporated by reference herein.

FIELD OF THE INVENTION

The present invention concerns novel compositions useful in cosmetic treatment of the skin or in the treatment of dermatological diseases.

TECHNICAL BACKGROUND

Properties of numerous compounds of animal or plant origin able to be beneficial for man or animal have been evidenced.

For example, the document by Jean Soon Park et al., *Astaxanthin decreased oxidative stress and inflammation and enhanced immune response in humans*, Nutr Metab (Lond), 2010, 7:18, discloses that a food diet of astaxanthin increases both humoral immune response and cell-mediated immune response in young healthy women.

The document by P. P. Ward et al., *Multifunctional roles of lactoferrin: a critical overview*, Cell. Mol. Life Sci., 2005, vol. 62, p. 2540-2548, describes different functions of lactoferrin such as iron capture in the intestines, antimicrobial action, anti-inflammatory function, protection against cancer and a role in bone morphogenesis.

The document by Didier Levieux, *Le colostrum, un lait particulièrement riche en de nombreux composants: peut-on en déceler la présence dans les livraisons de lait de vache?*, Lait, 1999, vol. 75, p. 465-488 (Colostrum, a milk particularly rich in numerous components: can the presence thereof be detected in cow milk deliveries?) describes the components of bovine colostrum, and the document by Sylvie F. Gauthier et al., *Growth factors from bovine milk and colostrum: composition, extraction and biological activities*, Lait, 2006, vol. 86, p. 99-125 lists the growth factors contained in colostrum and in milk and describes the properties thereof.

However, the beneficial properties of these components are essentially known when part of food intake.

For a variety of cosmetological and dermatological applications, there is a need to provide a composition allowing the lifetime of epidermal cells to be extended, in particular to slow skin atrophy.

SUMMARY OF THE INVENTION

The invention first concerns a composition comprising an iron-binding glycoprotein and a casein hydrolysate.

In some embodiments, the iron-binding glycoprotein is lactoferrin and/or the casein hydrolysate is α-casozepine or a fragment thereof having a size greater than or equal to 5 amino acid residues.

In some embodiments, the composition further comprises:
colostrum, preferably bovine colostrum, ovine colostrum, equine colostrum or porcine colostrum, more preferably bovine colostrum; and/or
a precursor of nitric oxide, preferably L-arginine;
an antioxidant, preferably a carotenoid, more preferably astaxanthin; and/or
serotonin or one of the precursors thereof which is preferably tryptophan.

In some embodiments, by weight of dry matter, the composition comprises:
from 2 to 30%, preferably 10 to 30% of iron-binding glycoprotein; and/or
from 2 to 30%, preferably 3 to 20% of casein hydrolysate; and/or
from 15 to 70%, preferably 20 to 50% of colostrum; and/or
from 10 to 50%, preferably 15 to 40% of nitric oxide precursor; and/or
from 2 to 30%, preferably 3 to 20% of antioxidant; and/or
from 2 to 30%, preferably 3 to 20% of serotonin or precursor thereof.

In some embodiments, by weight of dry matter, the composition comprises:
from 2 to 30%, preferably 10 to 30% of lactoferrin; and/or
from 2 to 30%, preferably 3 to 20% of α-casozepine; and/or
from 15 to 70%, preferably 20 to 50% of colostrum; and/or
from 10 to 50%, preferably 15 to 40% of L-arginine; and/or
from 2 to 30%, preferably 3 to 20% of astaxanthin; and/or
from 2 to 30%, preferably 3 to 20% of tryptophan.

In some embodiments, by weight of dry matter, the composition comprises:
from 15 to 20% of lactoferrin;
from 5 to 10% of α-casozepine;
from 25 to 45% of colostrum;
from 20 to 30% of L-arginine;
from 5 to 10% of astaxanthin; and
from 5 to 10% of tryptophan.

The invention also concerns a method for cosmetic treatment of the skin, comprising the topical application of a composition such as described above.

In some embodiments, the cosmetic treatment of the skin concerns filling wrinkles, reducing under-eye bags, lightening under-eye dark circles, reducing age spots, increasing skin elasticity and/or attenuating stretch marks.

The invention also concerns the composition such as described above for use thereof in the treatment of dermatological diseases.

In some embodiments, the composition is intended to be used in the treatment of skin atrophy, eczema and/or cheloids.

The present invention makes it possible to meet the above need. More particularly, it provides a composition allowing an increase in the size of keratinocytes. Therefore, the composition of the invention allows strengthening of skin cells, delayed degeneration thereof and hence an increase in their lifetime.

This is achieved chiefly through the association of two compounds: an iron-binding glycoprotein and a casein hydrolysate; and in some preferred embodiments through the association of these compounds with additional compounds.

DESCRIPTION OF EMBODIMENTS OF THE INVENTION

The invention is now described in more detail and in a non-limiting way in the description which follows. In the present description, unless otherwise expressly stated, all indicated percentages (%) are weight percentages.

In the present application, the term «iron-binding glycoprotein» is to be understood as meaning «one or more iron-binding glycoproteins» and «casein hydrolysate» is to be understood as meaning «one or more casein hydrolysates». The same applies to the other compounds of the composition.

Composition

The invention concerns a composition comprising an iron-binding glycoprotein (compound A) and a casein hydrolysate (compound B).

Preferably, the iron-binding glycoprotein is lactoferrin. Lactoferrin is a protein contained in milk whey, for example in human or bovine milk. Lactoferrin is a multifunctional glycoprotein playing a part in the preserving of cells against intrinsic attack. It affects the proliferation, maturation and activation of several types of immune cells and plays a role in the regulation, maturation and activation of neutrophils and macrophages, and in the maturation and function of lymphocytes. Lactoferrin also allows modulation of the immune function by promoting the action of cytokines. When colostrum is contained in the composition, lactoferrin enhances the action thereof.

Preferably, the casein hydrolysate is a hydrolysate of $\alpha_{s1}$ casein. More preferably, the casein hydrolysate is α-casozepine or a fragment thereof (having a size greater than or equal to 5 amino acid residues). α-casozepine is the decapeptide de SEQ ID NO. 1. Examples of fragments of α-casozepine that can be used in the invention are the nonapeptide of SEQ ID NO. 2, the octapeptide of SEQ ID NO. 3, the heptapeptide of SEQ ID NO. 4, the hexapeptide of SEQ ID NO.5 and the pentapeptide of SEQ ID NO. 6. α-casozepine and the abovementioned fragments have tranquilizing properties. They increase the activity of gamma-aminobutyric acid (GABA), a neurotransmitter having inhibitory action against anxiety and relaxing properties promoting a decrease in blood pressure.

The casein hydrolysate preferably has a molecular weight of 500 to 2000 Da, preferably of 1000 to 1500 Da.

The composition advantageously comprises from 5 to 50 weight %, preferably from 10 to 30 weight %, more preferably from 15 to 20 weight % of iron-binding glycoprotein, preferably lactoferrin, relative to the total weight of the composition.

The composition may comprise from 2 to 30 weight %, preferably from 3 to 20 weight %, more preferably from 5 to 10 weight % of casein hydrolysate, preferably α-casozepine or a fragment thereof, relative to the total weight of the composition.

The weight ratio of iron-binding glycoprotein to casein hydrolysate is advantageously from 0.1 to 6, preferably from 0.5 to 3, more preferably it is 2. In some embodiments, the weight ratio of iron-binding glycoprotein to casein hydrolysate is from 0.1 to 0.2, or from 0.2 to 0.3, or from 0.3 to 0.4, or from 0.4 to 0.5, or from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5, or from 5 to 6.

The composition may further comprise colostrum (compound C), for example bovine, ovine, equine or porcine colostrum. Preferably, the colostrum is bovine. Colostrum is the milk secreted by female mammalians just after giving birth. It comprises numerous components including the immunoglobulins IgG1, IGg2, IgM, IgA, lactoferrin, serum albumin, transferrin and α1-acid glycoprotein. Colostrum has energising properties. It enables the cells to fight against intrinsic and extrinsic attack and to maintain their vitality for a longer time. It reinforces cell membranes.

For example, the composition may comprise from 15 to 70 weight %, preferably from 20 to 50 weight %, more preferably from 25 to 40 weight % of colostrum dry matter relative to the total weight of the composition.

The weight ratio of colostrum dry matter relative to the casein hydrolysate is advantageously from 0.5 to 10, preferably from 1 to 6, more preferably it is 4. In some embodiments, the weight ratio of colostrum relative to the casein hydrolysate is from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5, or from 5 to 6, or from 6 to 7, or from 7 to 8, or from 8 to 9, or from 9 to 10.

It is to be understood here that the above weight amounts and ratios of colostrum dry matter relate to the total weight of the compounds of colostrum dry matter, excluding those compounds which are also included in the composition via specific addition. Thus, the weight of colostrum dry matter does not take into account the weight of lactoferrin contributed by colostrum (which is counted separately). However, in the composition of the invention the amount of lactoferrin contributed by colostrum is generally negligible compared with the total amount of colostrum dry matter.

In some embodiments, the composition further comprises a precursor of nitric oxide (compound D), preferably L-arginine. Nitric oxide is a signalling molecule with the function of dilating blood vessels. The precursor of nitric oxide facilitates migration of the other compounds in the composition into the skin. In particular, when colostrum is contained in the composition, the precursor of nitric oxide allows facilitated penetration of colostrum compounds into the skin. In addition, arginine is capable of stimulating the cells so that they produce more proteins such as collagen and elastin and are able to repair damaged genetic inheritance.

The composition may comprise from 10 to 50 weight %, preferably from 15 to 40 weight %, more preferably from 20 to 30 weight % of nitric oxide precursor relative to the total weight of the composition.

The weight ratio of the precursor of nitric oxide to the casein hydrolysate is advantageously from 0.1 to 10, preferably from 1 to 5, more preferably it is 3. In some embodiments, the weight ratio of the precursor of nitric oxide to the casein hydrolysate is from 0.1 to 0.2, or from 0.2 to 0.3, or from 0.3 to 0.4, or from 0.4 to 0.5, or from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5, or from 5 to 6, or from 6 to 7, or from 7 to 8, or from 8 to 9, or from 9 to 10.

An antioxidant can also be included in the composition (compound E), preferably a carotenoid. In particularly preferred manner, the antioxidant is astaxanthin. Astaxanthin has anti-inflammatory and antioxidant action and protects the mitochondrial double-membrane by improving the functions thereof and thereby increasing the capacity of mitochondria to produce energy. It can travel throughout the entire body providing antioxidant and anti-inflammatory action to all organs and tissues. It also reinforces the cell membrane.

Alternatively, or in combination with a carotenoid e.g. astaxanthin, the antioxidant can be a retinoid such as retinol, vitamin C (ascorbic acid and salts thereof) and/or vitamin E.

Preferably, in relation to the total weight of the composition, the antioxidant is contained in an amount of 2 to 30 weight %, preferably from 3 to 20 weight %, more preferably from 5 to 10 weight %.

The weight ratio of antioxidant to the casein hydrolysate is advantageously from 0.1 to 5, preferably from 0.5 to 3, more preferably it is 1. In some embodiments, the weight ratio of antioxidant to the casein hydrolysate is from 0.1 to 0.2, or from 0.2 to 0.3, or from 0.3 to 0.4, or from 0.4 to 0.5, or from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5.

The composition may further comprise serotonin or one of the precursors thereof (compound F). Preferably, the composition comprises a precursor of serotonin, and more preferably tryptophan, further preferably L-tryptophan. Serotonin and the precursors thereof, including tryptophan, have tranquilizing properties and play a role in depression, anxiety, mood and control of appetite. The use of a precursor of serotonin such as tryptophan is particularly advantageous since serotonin is incapable of passing through the blood-brain barrier whereas a precursor such as tryptophan has this capability. In addition, tryptophan can potentialize the action of the casein hydrolysate. It takes part in the formation of active lymphocytes of the body's defence system and acts on cellular stress.

The composition may comprise from 2 to 30 weight %, preferably from 3 to 20 weight %, more preferably from 5 to 10 weight % of serotonin or one of the precursors thereof, relative to the total weight of the composition.

The weight ratio of serotonin or one of the precursors thereof to the casein hydrolysate is advantageously from 0.1 to 5, preferably from 0.5 to 3, more preferably it is 1. In some embodiments, the weight ratio of serotonin or one of the precursors thereof to the casein hydrolysate is from 0.1 to 0.2, or from 0.2 to 0.3, or from 0.3 to 0.4, or from 0.4 to 0.5, or from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5.

In some embodiments, the composition further comprises at least one mineral filler, preferably a clay, more preferably selected from among illite, montmorillonite, kaolinite, or a mixture thereof. In particularly preferred manner, the composition comprises a mixture of illite, montmorillonite and kaolinite.

When the composition comprises a mineral filler, this is advantageously contained in an amount of 5 to 80 weight %, preferably from 10 to 50 weight % relative to the total weight of the composition.

The weight ratio of mineral filler to the casein hydrolysate is advantageously from 0.1 to 10, preferably from 0.5 to 5. In some embodiments, the weight ratio of mineral filler to the casein hydrolysate is from 0.1 to 0.2, or from 0.2 to 0.3, or from 0.3 to 0.4, or from 0.4 to 0.5, or from 0.5 to 0.6, or from 0.6 to 0.7, or from 0.7 to 0.8, or from 0.8 to 0.9, or from 0.9 to 1, or from 1 to 2, or from 2 to 3, or from 3 to 4, or from 4 to 5, or from 5 to 6, or from 6 to 7, or from 7 to 8, or from 8 to 9, or from 9 to 10.

In some embodiments, the composition comprises the compounds A, B and C described above.

In some embodiments, the composition comprises the compounds A, B and D described above.

In some embodiments, the composition comprises the compounds A, B and E described above.

In some embodiments, the composition comprises the compounds A, B and F described above.

In some embodiments, the composition comprises the compounds A, B, C and D described above.

In some embodiments, the composition comprises the compounds A, B, C and E described above.

In some embodiments, the composition comprises the compounds A, B, C and F described above.

In some embodiments, the composition comprises the compounds A, B, D and E described above.

In some embodiments, the composition comprises the compounds A, B, D and F described above.

In some embodiments, the composition comprises the compounds A, B, E and F described above.

In some embodiments, the composition comprises the compounds A, B, C, D and E described above.

In some embodiments, the composition comprises the compounds A, B, C, D and F described above.

In some embodiments, the composition comprises the compounds A, B, C, E and F described above.

In some embodiments, the composition comprises the compounds A, B, D, E and F described above.

In some embodiments, the composition comprises the compounds A, B, C, D, E and F described above.

In some embodiments, the composition essentially consists of, even consists of the compounds A, B, and possibly C and/or D and/or E and/or F, and optionally a mineral filler and/or a vehicle and/or one or more formulation additives (thickener, pigment or colouring agent, etc.).

The composition is preferably formulated in powder form. Alternatively, it can be formulated in liquid form, in gel form e.g. an oily gel, a cream, a coating on a patch, or in the form of granules, these forms preferably being produced from a powder of the composition which is then formulated with a vehicle and formulation additives.

The composition is preferably a cosmetological or dermatological composition.

Preparation Method

The invention also concerns a method for preparing the above-described composition comprising the mixing, in one or more steps, of the iron-binding glycoprotein with the casein hydrolysate and optionally the colostrum and/or nitric oxide precursor and/or antioxidant and/or serotonin or the precursor thereof and/or clay and/or excipient.

Preferably, the iron-binding glycoprotein and/or casein hydrolysate and/or colostrum and/or nitric oxide precursor and/or antioxidant and/or serotonin or one of the precursors thereof and/or clay are integrated in powder form.

Advantageously, mixing is conducted at a temperature ranging from 12° C. to 25° C., more preferably at a temperature ranging from 15° C. to 20° C., further preferably at a temperature ranging from 17° C. to 19° C. Said temperatures allow the preserving of the qualities of the compounds and prevents degradation thereof.

Mixing is preferably performed under slow agitation.

Uses

The invention also concerns a method for the cosmetic treatment of the skin. This method comprises the topical application of a composition such as defined above.

In some embodiments, the cosmetic treatment comprises or consists of filling wrinkles, reducing under-eye bags, lightening under-eye dark circles, reducing age spots, increasing skin elasticity and/or attenuating stretch marks.

Preferably, the composition is applied for cosmetic treatment in an amount ranging from 0.1 mg/cm$^2$ skin to 50 mg/cm$^2$ skin, preferably from 0.5 mg/cm$^2$ skin to 20 mg/cm$^2$ skin, more preferably from 0.8 mg/cm$^2$ skin to 10 mg/cm$^2$ skin. In some embodiments, the composition is applied in an amount of 0.1 to 0.3 mg/cm$^2$ skin, or from 0.3 to 0.5 mg/cm$^2$ skin, or from 0.5 to 0.8 mg/cm$^2$ skin, or from 0.8 to 1 mg/cm$^2$ skin, or from 1 to 1.5 mg/cm$^2$ skin, or from 1.5 to 2 mg/cm$^2$ skin, or from 2 to 2.5 mg/cm$^2$ skin, or from 2.5 to 3 mg/cm$^2$ skin, or from 3 to 3.5 mg/cm$^2$ skin, or from 3.5 to 4 mg/cm$^2$ skin, or from 4 to 4.5 mg/cm$^2$ skin, or from 4.5 to 5 mg/cm$^2$ skin, or from 5 to 6 mg/cm$^2$ skin, or from 6 to 7 mg/cm² skin, or from 7 to 8 mg/cm² skin, or from 8 to 9 mg/cm² skin, or from 9 to 10 mg/cm² skin, or from 10 to 15 mg/cm² skin, or from 15 to 20 mg/cm² skin, or from 20 to 25 mg/cm² skin, or from 25 to 30 mg/cm² skin, or from 30 to 35 mg/cm² skin, or from 35 to 40 mg/cm² skin, or from 40 to 45 mg/cm² skin, or from 45 to 50 mg/cm² skin.

In particular, the composition can be applied once every two days, or once a day, or twice a day, or three times a day.

A further aspect of the invention is a composition such as described above for use thereof in the treatment of dermatological conditions.

Examples of dermatological conditions are skin atrophy, eczema and/or cheloids. The treatment of skin atrophy is preferred.

Preferably, the composition is administered via topical route. In this case, the composition is advantageously applied for dermatological treatment in an amount ranging from 0.1 mg/cm² skin to 50 mg/cm² skin, preferably from 0.5 mg/cm² skin to 20 mg/cm² skin, more preferably from 0.8 mg/cm² skin to 10 mg/cm² skin. In some embodiments, the composition is applied in an amount of 0.1 to 0.3 mg/cm² skin, or from 0.3 to 0.5 mg/cm² skin, or from 0.5 to 0.8 mg/cm² skin, or from 0.8 to 1 mg/cm² skin, or from 1 to 1.5 mg/cm² skin, or from 1.5 to 2 mg/cm² skin, or from 2 to 2.5 mg/cm² skin, or from 2.5 to 3 mg/cm² skin, or from 3 to 3.5 mg/cm² skin, or from 3.5 to 4 mg/cm² skin, or from 4 to 4.5 mg/cm² skin, or from 4.5 to 5 mg/cm² skin, or from 5 to 6 mg/cm² skin, or from 6 to 7 mg/cm² skin, or from 7 to 8 mg/cm² skin, or from 8 to 9 mg/cm² skin, or from 9 to 10 mg/cm² skin, or from 10 to 15 mg/cm² skin, or from 15 to 20 mg/cm² skin, or from 20 to 25 mg/cm² skin, or from 25 to 30 mg/cm² skin, or from 30 to 35 mg/cm² skin, or from 35 to 40 mg/cm² skin, or from 40 to 45 mg/cm² skin, or from 45 to 50 mg/cm² skin.

The composition can be applied once every two days, or once a day, or twice a day, or three, four or five times a day.

EXAMPLES

The following are nonlimiting examples illustrating the invention.

Example 1

Preparation of the Compositions

A composition (Product A) was prepared by mixing the following components in powder form:

| Components | Mass (g) per 12 g of composition | Component supplier |
| --- | --- | --- |
| Bovine colostrum containing 30% active G-immunoglobulins | 4 | INGREDIA France |
| L-arginine | 3 | UNIPEX/Ajinomoto |
| Lactoferrin | 2 | INGREDIA France |
| Alpha-casozepine | 1 | INGREDIA France |
| Astaxanthin | 1 | UNIPEX/Ajinomoto |
| Tryptophan | 1 | UNIPEX/Ajinomoto |

A composition (Product P2) was then prepared by diluting 15% of Product A in carboxymethylcellulose gel (CMC gel).

Preparation and Treatment of Explants

Nine explants of diameter 12 mm (±1 mm) were prepared from an abdominoplasty of a Caucasian female aged 50 years. The explants were placed under survival in BEM medium (BIO-EC's Explants Medium) at 37° C. in a humid atmosphere enriched with 5% $CO_2$.

The explants were divided into 3 batches as follows:

| Batch | Treatment | Number of explants | Day experimentation stopped |
| --- | --- | --- | --- |
| T0 (plasty control) | None | 3 | D0 |
| T (non-treated control) | None | 3 | D12 |
| LP2 | Product P2 | 3 | D12 |

D0 designates the starting day of experimentation and Dn designates the $n^{th}$ day after the start of experimentation.

At D0, D2, D3, D6, D8 and D10, product P2 was topically applied with a spatula in an amount of 2 mg/cm² onto the explants of the batch corresponding to LP2. The explants of the control batches (TO and T) did not receive any treatment with the exception of renewal of the culture medium. At D2, D3, D6, D8 and D10, one half of the culture medium was renewed (1 mL of BEM medium per well).

At D0, the three explants of batch TO were removed and cut in half. One of the two halves was fixed in buffered formol solution and the other half was frozen to −80° C. At D12, the explants of each batch T and LP2 were collected and treated in the same manner.

Explant Characterization Methods

Histological Treatments and Control of Cell Viability

After 24 h in buffered formol, the samples were dehydrated and impregnated with paraffin using a Leica TP 1020 automatic tissue processor. They were embedded in paraffin at a Leica EG 1160 embedding station. 5 µm sections were obtained using a microtome of Minot type, Leica RM 2125, and mounted on Superfrost® histological glass slides. Microscopy observations were performed under optical microscopy using a Leica microscope of type DMLB or Olympus BX43. Images were taken with an Olympus DP72 camera and Cell^D software.

Cell viability was visualized on paraffin sections after staining with Masson's trichrome Goldner variant. It was evaluated by microscopic examination.

Measurement of Thickness of Epidermis Via Image Analysis.

Analysis of the images obtained after staining with Masson's trichrome stain was carried out for the purpose of measuring the thickness of the epidermis. Measurements were taken on three regions of interest per image, i.e. 27 measurements per batch.

Results

At D12, the cell viability of control batch T was fairly good in the epidermis and good in the dermis.

On the explants treated with product P2, an increase was observed in the thickness of the epidermis caused by hypertrophic acanthosis (increase in epidermal thickness due to an increase in the size of the keratinocytes). The cells are larger, translating increased nutritional uptake in the cells.

Measurements of the thickness of the epidermis are summarised in the table below:

| Batch | T0 | T | LP2 |
| --- | --- | --- | --- |
| Measurement day | D0 | D12 | D12 |
| Mean thickness of epidermis (µm) | 28.5 | 50.3 | 66.1 |
| Standard deviation | 4.6 | 7.3 | 6.9 |

Application of product P2 induced a significant increase in the thickness of the epidermis by 31% compared with the nontreated control epidermis (p<0.01).

The cells of the explants treated with product P2 are larger than the cells of the nontreated control explants. They are in good condition to withstand various biological and environmental stresses. In addition, cell lifetime is also improved.

Example 2

Preparation of the Products.

The following compositions were prepared:
Product P1': lactoferrin (powder) diluted to a final concentration of 15 weight % in carboxymethylcellulose gel (CMC gel);
Product P2': alpha-casozepine (powder) diluted to a final concentration of 15 weight % in CMC gel;
Product P3': mixture of lactoferrin and alpha-casozepine (powder) diluted to a final concentration of 15 weight % in CMC gel;
Product P4': product A such as described above in Example 1 (powder) diluted to a final concentration of 15 weight % in CMC gel.

Products P3' and P4' are compositions of the invention, products P1' and P2' are comparative examples.

Preparation and Treatment of the Explants 18 explants of diameter 12 mm (±1 mm) were prepared from an abdominoplasty of a Caucasian female aged 45 years. The explants were placed in BEM survival medium (BIO-EC's Explants Medium) at 37° C. in a humid atmosphere enriched with 5% $CO_2$.

The explants were divided into 6 batches as follows:

| Batch | Treatment | Number of explants | Day experimentation stopped |
|---|---|---|---|
| T0' (plasty control) | None | 3 | D0 |
| T' (non-treated control) | None | 3 | D18 |
| LP1' | Product P1' | 3 | D18 |
| LP2' | Product P2' | 3 | D18 |
| LP3' | Product P3' | 3 | D18 |
| LP4' | Product P4' | 3 | D18 |

D0 designates the starting day of experimentation and Dn designates the $n^{th}$ day after the start of experimentation.

At D0, D2, D3, D6, D8, D10, D13, D15 and D17, the products P1', P2', P3' and P4' were topically applied in an amount of 2 μL per explant and spread with a spatula onto the explants of batches LP1', LP2', LP3' and LP4' respectively. The explants of the control batches (T0' and T') did not receive any treatment with the exception of renewal of the culture medium. At D2, D3, D6, D8, D10, D13, D15 and D17, one half of the culture medium was renewed (1 mL of BEM medium per well).

At D0, the three explants of batch T0' were removed and cut in half. One of the halves was fixed in buffered formol solution, and the other half was frozen and stored at −80° C. At D18, the explants of each batch T', LP1', LP2', LP3' and LP4' were removed and treated in similar manner.

Explant Characterization Methods

Control of cell viability and measurement of thickness of the epidermis were carried out as described in Example 1.

Examination of general morphology was performed in the same manner as examination of cell viability, i.e. general morphology was assessed on paraffin sections after staining with Masson's trichrome-Goldner variant, under a microscope.

Results

At D0, on the control plasty batch T0', cell viability was good in the epidermis and good in the dermis. The relief of the dermal-epidermal junction (DEJ) was fairly well-defined and the density of the dermis was distinct.

At D18, on the non-treated control batch T', cell viability was distinctly impaired in the epidermis and very slightly impaired in the dermis. The relief of the dermal-epidermal junction (DEJ) was moderate and dermal density was thin.

The following effects on the general morphology of the explants were observed at D18 further to application of products P1', P2', P3' and P4', compared with the control batch T' at D18.

Application of product P1' induces a slight improvement in the cell viability of the epidermis and a very slight improvement in the dermis. In addition, it induces a slight increase in the thickness of the epidermis caused by hypertrophic acanthosis. Finally, it induces a slight increase in dermal density.

Application of product P2' induces a very slight improvement in the cell viability of the dermis, but no change in the epidermis. In addition, it induces a slight increase in the thickness of the epidermis caused by hypertrophic acanthosis. Finally, it induces a slight increase in dermal density.

Application of product P3' induces a slight improvement in the cell viability of the epidermis and a very slight improvement in the dermis. In addition, it induces a moderate increase in the thickness of the epidermis caused by hypertrophic acanthosis. Finally, it induces a slight increase in dermal density.

Application of product P4' induces a moderate improvement in the cell viability of the epidermis and a very slight improvement in the dermis. In addition, it induces a moderate increase in the thickness of the epidermis caused by hypertrophic acanthosis. Finally, it induces a moderate increase in dermal density.

Measurements of the thickness of the epidermis are summarised in the table below:

| Batch | T0' | T' | LP1' | LP2' | LP3' | LP4' |
|---|---|---|---|---|---|---|
| Day of measurement | D 0 | D 18 | D 18 | D 18 | D 18 | D 18 |
| Mean thickness of epidermis (μm) | 33.6 | 32.5 | 37.5 | 38.6 | 41.1 | 41.5 |
| Standard deviation | 4.8 | 6.2 | 4.9 | 5.0 | 6.7 | 7.7 |
| Increase in thickness of epidermis compared with batch T' at D 18 (%) | — | — | 15* | 19* | 26* | 28* |

*= significant value, with p <0.01

Application of product P3' induces an increase in the thickness of the epidermis that is distinctly greater than that obtained with products P1' and P2'. Product P3' therefore has better anti-ageing action than products P1' and P2'. In addition, compared with product P2', product P3' improves cell viability.

Application of product P4' also induces an increase in the thickness of the epidermis that is distinctly greater than that obtained with products P1' and P2'. Product P4' therefore has better anti-ageing action than products P1' and P2'. In addition, compared with products P1', P2' and P3', application of product P4' improves cell viability and dermal density.

What is claimed is:

1. A composition for topical application comprising lactoferrin, α-casozepine, and carboxymethylcellulose gel, wherein the weight ratio of lactoferrin to α-casozepine is from 0.1 to 6.

2. The composition according to claim 1, further comprising colostrum.

3. The composition according to claim 1 comprising, by weight of dry matter one or more components selected from the group consisting of:
   from 2 to 30% by weight of dry matter, of actoferrin;
   from 2 to 30% by weight of dry matter, of α-casozepine;
   from 15 to 70% by weight of dry matter, of colostrum;
   from 10 to 50% by weight of dry matter, of nitric oxide precursor;

from 2 to 30% by weight of dry matter, of antioxidant; and
from 2 to 30% by weight of dry matter, of serotonin or a precursor thereof.

4. The composition according to claim 1 comprising, by weight of dry matter one or more components selected from the group consisting of:
from 2 to 30% by weight of dry matter of lactoferrin;
from 2 to 30% by weight of dry matter of α-casozepine;
from 15 to 70% by weight of dry matter of colostrum;
from 10 to 50% by weight of dry matter of L-arginine;
from 2 to 30% by weight of dry matter of astaxanthin; and
from 2 to 30% by weight of dry matter of tryptophan.

5. The composition according to claim 1, comprising by weight of dry matter:
from 15 to 20% of lactoferrin;
from 5 to 10% of α-casozepine;
from 25 to 45% of colostrum;
from 20 to 30% of L-arginine;
from 5 to 10% of astaxanthin; and
from 5 to 10% of tryptophan.

6. A method for cosmetic treatment of the skin, comprising topically applying to the skin the composition according to claim 1.

7. The method according to claim 6, wherein the cosmetic treatment of the skin is selected from the group consisting of: filling wrinkles, reducing under-eye bags, lightening under-eye dark circles, reducing age spots, increasing skin elasticity and attenuating stretch marks.

8. A method for treatment of a dermatological disease comprising administering the composition according to claim 1 to a patient in need thereof.

9. The method according to claim 8, wherein the dermatological disease is selected from the group consisting of: skin atrophy, eczema and cheloids.

10. The composition according to claim 2, wherein the colostrum is bovine colostrum.

11. The composition according to claim 1, further comprising a precursor of nitric oxide.

12. The composition according to claim 11, wherein the precursor of nitric oxide is L-arginine.

13. The composition according to claim 1, further comprising an antioxidant.

14. The composition according to claim 13, wherein the antioxidant is astaxanthin.

15. The composition according to claim 1, further comprising serotonin or a precursor thereof.

16. The composition according to claim 15, wherein the serotonin or precursor thereof is tryptophan.

17. The composition according to claim 1 comprising, by weight of dry matter one or more components selected from the group consisting of:
from 10 to 30% by weight of dry matter of actoferrin;
from 3 to 20% by weight of dry matter of α-casozepine;
from 20 to 50% by weight of dry matter of colostrum;
from 15 to 40% by weight of dry matter of nitric oxide precursor;
from 3 to 20% by weight of dry matter of antioxidant; and
from 3 to 20% by weight of dry matter of serotonin or a precursor thereof.

18. The composition according to claim 1 comprising, by weight of dry matter one or more components selected from the group consisting of:
from 10 to 30% by weight of dry matter of lactoferrin;
from 3 to 20% by weight of dry matter of α-casozepine;
from 20 to 50% by weight of dry matter of colostrum;
from 15 to 40% by weight of dry matter of L-arginine;
from 3 to 20% by weight of dry matter of astaxanthin; and
from 3 to 20% by weight of dry matter of tryptophan.

* * * * *

SEQUENCE LISTING

```
<160> NUMBER OF SEQ ID NOS: 6

<210> SEQ ID NO 1
<211> LENGTH: 10
<212> TYPE: PRT
<213> ORGANISM: Bos taurus

<400> SEQUENCE: 1

Tyr Leu Gly Tyr Leu Glu Gln Leu Leu Arg
1               5                   10

<210> SEQ ID NO 2
<211> LENGTH: 9
<212> TYPE: PRT
<213> ORGANISM: Bos taurus

<400> SEQUENCE: 2

Tyr Leu Gly Tyr Leu Glu Gln Leu Leu
1               5

<210> SEQ ID NO 3
<211> LENGTH: 8
<212> TYPE: PRT
<213> ORGANISM: Bos taurus

<400> SEQUENCE: 3

Tyr Leu Gly Tyr Leu Glu Gln Leu
1               5

<210> SEQ ID NO 4
<211> LENGTH: 7
<212> TYPE: PRT
<213> ORGANISM: Bos taurus

<400> SEQUENCE: 4

Tyr Leu Gly Tyr Leu Glu Gln
1               5

<210> SEQ ID NO 5
<211> LENGTH: 6
<212> TYPE: PRT
<213> ORGANISM: Bos taurus

<400> SEQUENCE: 5

Tyr Leu Gly Tyr Leu Glu
1               5

<210> SEQ ID NO 6
<211> LENGTH: 5
<212> TYPE: PRT
<213> ORGANISM: Bos taurus

<400> SEQUENCE: 6

Tyr Leu Gly Tyr Leu
1               5
```